United States Patent
Bernard et al.

(10) Patent No.: US 9,238,014 B2
(45) Date of Patent: Jan. 19, 2016

(54) PHARMACEUTICAL COMPOSITION FOR TREATING ALCOHOL DEPENDENCY

(76) Inventors: Philippe Bernard, La Ferte Saint Aubin (FR); Fabrice Trovero, Avaray (FR)

( * ) Notice: Subject to any disclaimer, the term of this patent is extended or adjusted under 35 U.S.C. 154(b) by 25 days.

(21) Appl. No.: 13/519,042

(22) PCT Filed: Dec. 29, 2010

(86) PCT No.: PCT/FR2010/052932
§ 371 (c)(1),
(2), (4) Date: Jul. 26, 2012

(87) PCT Pub. No.: WO2011/080488
PCT Pub. Date: Jul. 7, 2011

(65) Prior Publication Data
US 2012/0289514 A1  Nov. 15, 2012

(30) Foreign Application Priority Data
Dec. 30, 2009 (FR) ...................... 09 59669

(51) Int. Cl.
 *A61K 31/451* (2006.01)
 *A61K 31/517* (2006.01)
 *A61K 31/18* (2006.01)
(52) U.S. Cl.
 CPC ............... *A61K 31/18* (2013.01); *A61K 31/451* (2013.01); *A61K 31/517* (2013.01)
(58) Field of Classification Search
 None
 See application file for complete search history.

(56) References Cited

U.S. PATENT DOCUMENTS

2008/0194631 A1 * 8/2008 Trovero et al. ................ 514/325

FOREIGN PATENT DOCUMENTS

WO   2006018538 A1   2/2006

OTHER PUBLICATIONS

Chou TC. "Theoretical Basis, Experimental Design, and Computerized Simulation of Synergism and Antagonism in Drug Combination Studies". Pharmacological Reviews, vol. 58: 621-681, 2006.*
Esteban et al., "Reduced Ethanol Consumption During Cyproheptadine Administration in Rats from a Long-term Alcohol-treated Colony", Physiol & Behavior 38(2):247-254 (1986).
Simpson et al., "A Pilot Trial of the Alpha-1 Adrenergic Antagonist, Prazosin, for Alcohol Dependence", Alcohol Clin Exp Res 33(6):255-263 (2009).
Walker et al., "Alpha-Noradrenergic Receptor Antagonism Blocks Dependence-Induced Increases in Responding for Ethanol", Alcohol 42(2):91-97 (2008).

* cited by examiner

*Primary Examiner* — Svetlana M Ivanova
(74) *Attorney, Agent, or Firm* — Porzio, Bromberg & Newman, P.C.

(57) ABSTRACT

Pharmaceutical composition for treating alcohol dependence in humans comprising two active ingredients:
 a compound having an antagonistic action on the 5-HT2 serotoninergic receptors selected as being cyproheptadine; and
 a compound having an antagonistic action on the alpha1-noradrenergic receptors selected from prazosin, alfuzosin, terazosin and tamsulosin.

8 Claims, No Drawings

PHARMACEUTICAL COMPOSITION FOR TREATING ALCOHOL DEPENDENCY

CROSS REFERENCE TO RELATED APPLICATION

This is a National Stage of International Application No. PCT/PR2010/052932, filed 29 Dec. 2010, which claims the benefit of Application No. 09/59669, filed in France on 30 Dec. 2009, the disclosures of which Applications are incorporated by reference herein.

The present invention relates to a pharmaceutical composition that can be used for treating alcohol dependence.

The pharmacological treatment of phenomena of dependence, including alcohol dependence, is a major challenge in public health. For a very long time, treatment of dependence on various addictive substances such as alcohol has mainly been directed at aiding withdrawal, i.e. cessation of consumption. This therapeutic strategy has therefore concentrated on reducing the physical symptoms that reflect the state of withdrawal at the time of cessation. These symptoms, which characterize physical dependence, are a function of the products consumed: in the context of alcohol dependence, they are manifested by tremors. Withdrawal also triggers behavioral disorders (anxiety, irascibility, agitation etc.).

In the context of the treatment of drug addiction, the existing pharmacopoeia has therefore developed around substitution products, for which the main therapeutic objective is to limit the physical symptoms induced by withdrawal. However, there are few if any substances that aim to counteract the states of psychic dependence, i.e. the irrepressible need (or "craving") for alcohol. This state of psychic dependence is much more robust and is generally the cause of relapses.

At the date of the present invention, pharmacological treatments have been or are proposed in the context of treatment of alcohol dependence.

Among these treatments, we may mention the use of opiate antagonists, which stimulate the activity of the dopaminergic systems. Opioid systems play a crucial role in the development of alcohol dependence by contributing to the euphorigenic and appetitive effects from drinking alcohol.

Naltrexone, an opiate antagonist, has been tested in clinical trials. Studies have shown that naltrexone reduces alcohol consumption, the relapse rate and the desire to drink, especially in the case of severe alcoholization. It is therefore the first pharmacological agent against alcoholism that acts otherwise than by triggering an effect of aversion.

Unfortunately, the use of naltrexone is limited on account of its gastrointestinal side effects (nausea, vomiting, loss of appetite) (O'Malley et al., 1992, *Naltrexone and coping skills therapy for alcohol dependence, A controlled study, Arch Gen Psychiatry*; 1992, 49; p 881-7; Volpicelli et al., *Naltrexone in the treatment of alcohol dependence*, Arch Gen Psychiatry, 1992, 49, p 876-80; Kranzler et al., *Naltrexone vs. Nefazodone for Treatment of Alcohol Dependence—A Placebo-Controlled Trial*; Neuropsychopharmacology, 2000, 22, 5, p 493-503).

Mention may also be made of the use of naltrindole, a δ-opiate receptor antagonist, which has shown some efficacy in animal models.

The use of acamprosate has also been considered. Although its mechanism of action has not been elucidated fully, there is a good deal of evidence suggesting that acamprosate acts by modulation of glutamatergic transmission. The molecule would appear to be effective, at least in the treatment of withdrawal symptoms. Its efficacy with respect to craving for alcohol is still under discussion.

Serotoninergic antidepressants have also been used. Serotoninergic transmission plays an important role in the pathophysiology of alcohol dependence. Serotonin re-uptake inhibitors are antidepressants that have been tested in the treatment of alcoholism (Naranjo et al., *Zimelidine-induced variations in alcohol intake by nondepressed heavy drinkers;* Clin Pharmacol Ther, 1984 35, p 374-81; Naranjo et al., *The serotonin uptake inhibitor citalopram attenuates ethanol intake,* Clin Pharmacol Ther, 1987, 41, p 266-74; Naranjo et al., *Fluoxetine differentially alters alcohol intake and other consummatory behaviors in problem drinkers*, Clin Pharmacol Ther, 1990, 47, p 490-8). Therapeutic trials based on these serotoninergic substances have given variable results, and clinical studies have not demonstrated any real efficacy.

Mention may be made of the use of benzodiazepines, the drugs that are most used for alcohol withdrawal (Lejoyeux et al. *Benzodiazepine treatment for alcohol-dependent patients*, Alcohol & Alcoholism, 1998, Vol. 33. No.6. Pp. 563-575). Benzodiazepines are effective when used at the time of withdrawal. Long-term efficacy is controversial, especially as patients follow this type of treatment for long periods to combat symptoms of abstinence such as anxiety and insomnia. There is the question of the benefit/risk ratio, to the extent that it is a matter of replacing one product of abuse with another, in a patient who is already susceptible to phenomena of dependence.

Finally, we may mention the use of aversion drugs. Thus, the first aversion drug against alcohol was disulfiram, used since 1940. When it is taken simultaneously with alcohol, this product triggers unpleasant effects such as nausea, vomiting, an increase in blood pressure and heart rate.

At the date of the present invention, there is therefore still a need to develop new treatments for combating alcohol dependence.

Cyproheptadine denotes 4-(5H-dibenzo[a,d]cyclohepten-5-ylidene)-1-methylpiperidine hydrochloride of formula:

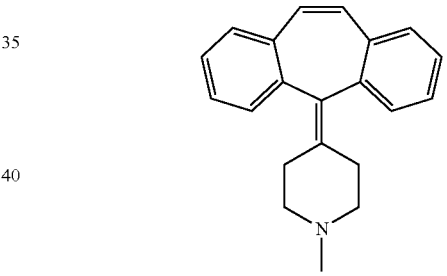

This active ingredient is known to have an antagonistic action on the 5-HT2 serotoninergic receptors and is usually employed as antihistamine/anticholinergic and antiserotoninergic. Marketed under the name Périactine®, it is recommended for symptomatic treatment of various allergic manifestations.

Prazosin denotes 2-[4-(2-furoyl)piperazin-1-yl]-6,7-dimethoxyquinazolin-4-amine of formula:

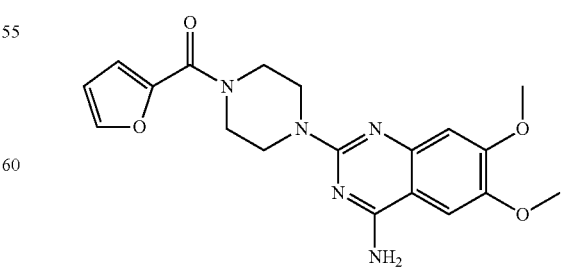

This active ingredient is known to have an antagonistic action on the alpha1-noradrenergic receptors and is usually employed as an antihypertensive. Marketed under the name Minipress®, it is recommended for treating arterial hypertension, and congestive left ventricular failure, but also in the context of symptomatic treatment of Raynaud phenomena (primary or secondary) and certain functional manifestations associated with benign prostatic hypertrophy.

The possible use of prazosin alone for treating alcohol dependence was reported by Tracy L. Simpson et al. in *A Pilot Trial of the Alpha-1 Adrenergic Antagonist, Prazosin, for Alcohol Dependence*, Alcoholism: Clinical and Experimental Research, Vol. 32, No. 11, November 2008, pp. 1-9. However, in the context of this study, the doses of prazosin administered were 4 mg in the morning, 4 mg at midday and 8 mg in the evening, i.e. a daily dose of 16 mg.

This dose is much higher than the maximum recommended therapeutic dose of 10 mg of prazosin daily, and moreover is very close to the maximum dose that should not be exceeded, i.e. 20 mg daily. At these doses, the first side effects appear, such as orthostatic vertigo, fatigue and somnolence. Moreover, the authors themselves share their reservations about the results obtained during this clinical study in view of the small number of subjects (7 patients treated) and the short duration of the clinical trial (6 weeks) for finding a therapeutic benefit for the phenomenon of dependence, which is mainly judged from the risks of relapse in the medium and short term. In man, the critical period of relapse is in fact at least one year of abstinence.

Alfuzosin denotes N-[3-[(4-amino-6,7-dimethoxy-quinazolin-2-yl)-methyl-amino]propyl]tetrahydrofuran-2-carboxamide of formula:

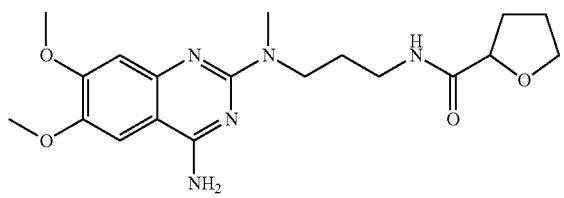 [SMILES: COc1cc2nc(N(C)CCCNC(=O)C3CCCO3)nc(N)c2cc1OC]

This active ingredient is known to have an antagonistic action on the alpha1-noradrenergic receptors. Marketed under the name Urion®, it is recommended for treating the functional symptoms of benign hypertrophy of the prostate.

Terazosin denotes 6,7-dimethoxy-2-[4-(tetrahydrofuran-2-ylcarbonyl)piperazin-1-yl]quinazolin-4-amine of formula:

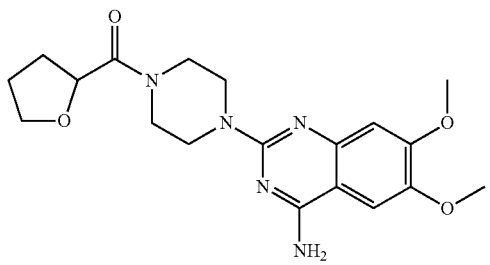 [SMILES: COc1cc2nc(N3CCN(C(=O)C4CCCO4)CC3)nc(N)c2cc1OC]

This active ingredient is known to have an antagonistic action on the alpha1-noradrenergic receptors. Marketed under the name Hytrine® or Dysalfa®, it is recommended for treating the functional symptoms of benign hypertrophy of the prostate.

Tamsulosin denotes (R)-5-(2-(2-(2-ethoxyphenoxy)ethylamino)propyl)-2-methoxybenzenesulfonamide of formula:

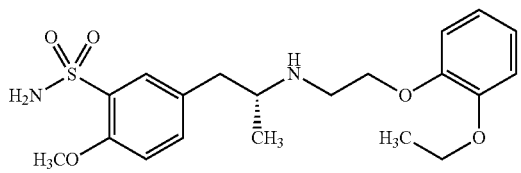 [SMILES: CCOc1ccccc1OCCN[C@H](C)Cc1ccc(OC)c(S(N)(=O)=O)c1]

This active ingredient is known to have an antagonistic action on the alpha1-noradrenergic receptors. Marketed under the name Josir® or Emix®, it is recommended for treating the functional symptoms of benign hypertrophy of the prostate.

Patent application WO 2006/018538 describes the use of combinations of active ingredients having a simultaneous antagonistic action on the alpha1-noradrenergic, NMDA glutamatergic and 5-HT2 serotoninergic receptors for treating disorders of the central nervous system such as drug dependence, psychoses, smoking addiction, disorders connected with alcohol consumption, schizophrenia, acute and chronic psychotic states, dementias, mood disorders, attention deficit disorders, sleep disorders, impulsivity disorders, hyperactivity, acute and chronic psychotic states, states of dependence on addictive substances, alcohol dependence, dependence on psychostimulants, dependence on opiates, dependence on benzodiazepines, dependence on tobacco and gambling addiction.

The composition comprising ifenprodil and cyproheptadine is preferred and has demonstrated activity in the context of treating amphetamine dependence.

The compositions described and tested in the context of this patent application must have a simultaneous antagonistic action on three receptors: the alpha1-noradrenergic receptors, the NMDA glutamatergic receptors and the 5-HT2 serotoninergic receptors.

Now, a simultaneous antagonistic action on these three receptors increases the risks of developing major side effects, in particular during prolonged treatments.

There is therefore a need to identify new pharmaceutical compositions having a therapeutic activity at least equivalent to the compositions already known but able to limit the risks of developing major side effects.

It was found, quite unexpectedly, that certain compounds having an antagonistic action on the alpha1-noradrenergic receptors could be used in combination with a compound having an antagonistic action on the 5-HT2 serotoninergic receptors in the context of treating alcohol dependence with an efficacy at least comparable, or even better, than the compositions described in the prior art. Moreover, synergy of activity was also observed during the combined use of certain compounds having an antagonistic action on the alpha1-noradrenergic receptors with a compound having an antagonistic action on the 5-HT2 serotoninergic receptors in the context of treating alcohol dependence in comparison with the activity of each of the compounds used separately.

Thus, the present invention relates to a pharmaceutical composition for treating alcohol dependence in humans comprising two active ingredients:
- a compound having an antagonistic action on the 5-HT2 serotoninergic receptors selected as being cyproheptadine; and
- a compound having an antagonistic action on the alpha1-noradrenergic receptors selected from prazosin, alfuzosin, terazosin and tamsulosin.

The pharmaceutical composition according to the invention makes it possible to limit the risks of developing major side effects by having a simultaneous antagonistic action on the alpha1-noradrenergic and 5-HT2 serotoninergic receptors, while maintaining an efficacy at least comparable to that of the pharmaceutical compositions that are known to have a simultaneous antagonistic action on the alpha1-noradrenergic, 5-HT2 serotoninergic and NMDA glutamatergic receptors. Moreover, the composition according to the invention showed unexpected synergy between the active ingredients.

In the context of the present invention:
"daily administration" means administration once daily or administration once per 24 hours; and
"continuous schedule" means continuous therapeutic treatment of a patient, comprising successive administration of one or more therapeutic compositions (including combination therapies, whether or not according to the invention), identical or different, each with its own regimen of therapeutic administration (number of daily administrations and number of days of administration over a given period, week for example) and without limit and not staggered or spread over time, i.e. without interruption of treatment;
"pharmaceutically acceptable salt" of an active ingredient means any salt of addition of said active ingredient with a mineral or organic acid by the action of said acid in an organic or aqueous solvent such as an alcohol, a ketone, an ether or a chlorinated solvent, and that is acceptable from the pharmaceutical standpoint;
"pharmaceutically acceptable derivative" of an active ingredient means any "prodrug" or "metabolite" of said active ingredient, as well as a pharmaceutically acceptable salt thereof;
"prodrug" of an active ingredient means any compound whose biotransformation in the body leads to said active ingredient;
"metabolite" of an active ingredient means any intermediate resulting from the transformation of said active ingredient in the body during a metabolic process;
cyproheptadine denotes (5H-dibenzo[a,d]cyclohepten-5-ylidene)-1-methylpiperidine hydrochloride, as well as pharmaceutically acceptable salts or derivatives thereof;
prazosin denotes 2-[4-(2-furoyl)piperazin-1-yl]-6,7-dimethoxyquinazolin-4-amine, as well as pharmaceutically acceptable salts or derivatives thereof;
alfuzosin denotes N-[3-[(4-amino-6,7-dimethoxyquinazolin-2-yl)-methyl-amino]propyl]tetrahydrofuran-2-carboxamide, as well as pharmaceutically acceptable salts or derivatives thereof;
terazosin denotes 6,7-dimethoxy-2-[4-(tetrahydrofuran-2-ylcarbonyl)piperazin-1-yl]quinazolin-4-amine, as well as pharmaceutically acceptable salts or derivatives thereof; and
tamsulosin denotes (R)-5-(2-(2-(2-ethoxyphenoxy)ethylamino)propyl)-2-methoxybenzenesulfonamide, as well as pharmaceutically acceptable salts or derivatives thereof.

Preferably, the present invention relates to a pharmaceutical composition as defined above, in which the compound having an antagonistic action on the alpha1-noradrenergic receptors is prazosin.

The pharmaceutical composition according to the present invention contains the active ingredients in a sufficient amount to ensure the desired therapeutic effect, i.e. treatment of alcohol dependence in the patient being treated.

Preferably, the following daily amounts of the active ingredients are used for preparing the pharmaceutical composition according to the invention:

from 0.04 to 20 mg of cyproheptadine, preferably from 0.4 to 10 mg of cyproheptadine;
from 0.025 to 20 mg of prazosin, preferably from 0.25 to 10 mg of prazosin;
from 0.075 to 10 mg of alfuzosin, preferably from 0.75 to 7.5 mg of alfuzosin;
from 0.01 to 5 mg of terazosin, preferably from 0.1 to 2.5 mg of terazosin;
from 0.004 to 0.4 mg of tamsulosin, preferably from 0.04 to 0.4 mg of tamsulosin.

The pharmaceutical composition according to the present invention can be formulated in any pharmaceutical form necessary for administration thereof. In particular, in the case of administration by the oral route, the compositions according to the present invention can be formulated in the form of coated or uncoated, effervescent, soluble, orodispersible, enteric or modified-release tablets; sugar-coated pills; hard capsules; soft capsules; granules; granulate; pills; pastilles. In the case of administration by the nasal route, the composition can be formulated in the form of spray or of powder to be inhaled. In the case of systemic administration, the composition according to the invention can be formulated in the form of sterile lyophilized powder for injection. The pharmaceutical compositions according to the present invention can therefore comprise, in addition to the active ingredients, any pharmaceutically acceptable formulation aid known by a person skilled in the art and that is necessary for preparing the pharmaceutical composition in the desired form.

The pharmaceutical composition according to the invention can be administered from one to four times daily, without exceeding the maximum daily dose. Thus, the present invention also relates to a pharmaceutical composition as defined above for administration 1 to 4 times daily to an alcohol-dependent patient.

The pharmaceutical composition according to the invention can be administered at any time of day, before, during or after meals, without affecting the efficacy of the treatment.

The pharmaceutical composition according to the present invention can be administered to the patient one or more times weekly. Thus, the present invention also relates to a pharmaceutical composition as defined above for daily administration for 1 to 7 days per week to an alcohol-dependent patient.

The composition according to the present invention can be administered according to a continuous schedule.

The present invention also relates to the use of a pharmaceutical composition as defined above for preparing a medicinal product intended for treating alcohol dependence in humans.

The present invention also relates to the use of a pharmaceutical composition as defined above for preparing a medicinal product intended for treating alcohol dependence in humans, said medicinal product being administered 1 to 4 times daily.

The present invention also relates to the use of a pharmaceutical composition as defined above for preparing a medicinal product intended for treating alcohol dependence in humans, said medicinal product being administered daily, 1 to 7 days per week.

The present invention also relates to a method of treating alcohol dependence in a human being by administration of a pharmaceutical composition as defined above.

The present invention also relates to a method of treating alcohol dependence in a human being by administration of a pharmaceutical composition as defined above 1 to 4 times daily.

The present invention also relates to a method of treating alcohol dependence in a human being by daily administration of a pharmaceutical composition as defined above 1 to 7 days per week, and administration can, but need not, be carried out according to a continuous schedule.

The two active ingredients making up the novel pharmaceutical composition according to the invention can be administered in the form of a unit pharmaceutical composition comprising the two active ingredients permitting administration of said composition to the patient in a single dose.

However, separate administration of the two active ingredients making up the novel pharmaceutical composition according to the invention can also be envisaged. Thus, the present invention also relates to a pharmaceutical product containing:
- a compound having an antagonistic action on the 5-HT2 serotoninergic receptors selected as being cyproheptadine; and
- a compound having an antagonistic action on the alpha1-noradrenergic receptors selected from prazosin, alfuzosin, terazosin and tamsulosin;

as a combination product (or pharmaceutical kit) for simultaneous, separate or spread over time administration for treating alcohol dependence in humans.

The pharmaceutical product according to the invention can of course be administered according to one of the administration regimens defined above. Thus, the present invention also relates to a pharmaceutical product containing:
- a compound having an antagonistic action on the 5-HT2 serotoninergic receptors selected as being cyproheptadine; and
- a compound having an antagonistic action on the alpha1-noradrenergic receptors selected from prazosin, alfuzosin, terazosin and tamsulosin;

as a combination product (or pharmaceutical kit) for simultaneous, separate or spread over time administration, 1 to 4 times daily, for treating alcohol dependence in humans.

The pharmaceutical product according to the invention can of course be administered according to one of the administration regimens defined above. Thus, the present invention also relates to a pharmaceutical product containing:
- a compound having an antagonistic action on the 5-HT2 serotoninergic receptors selected as being cyproheptadine; and
- a compound having an antagonistic action on the alpha1-noradrenergic receptors selected from prazosin, alfuzosin, terazosin and tamsulosin;

as a combination product (or pharmaceutical kit) for simultaneous, separate or spread over time administration, 1 to 7 days per week, for treating alcohol dependence in humans.

The present invention is illustrated by the following non-limiting examples.

EXAMPLE 1

Materials

The model used is alcohol consumption in the male mouse of the C57BL/6J line, which displays a considerable craving for alcohol. The protocol used is comparable to those used in previous studies (Grahame et al., 2000, *Naltrexone and alcohol drinking in mice lacking β-endorphin by site-direct mutagenesis*, Pharmacol Biochem Behav; 67; pp 759-766; Finn et al., 2005, *A procedure to produce high alcohol intake in mice;* Psychopharmacology 178; pp 471-480; Rhodes et al., 2005, *Evaluation of a simple model of ethanol drinking to intoxication in C57BL/6J mice,* Physiol Behav; 54; pp 53-63).

Products

All the products used for the treatments are dissolved in saline (0.9% NaCl) so that the injection volume is 10 ml/kg of body weight.

Prazosin was tested at the following doses: 1 mg/kg; 0.5 mg/kg.

Cyproheptadine was tested at the following dose: 1 mg/kg
Ifenprodil was tested at the following dose: 1 mg/kg Protocol for Measuring Alcohol Consumption The animals are kept in their cage throughout the experiment. They are subjected to forced alcoholization, with 10% alcohol as the only drink, for 15 days. They are then returned to normal conditions with water to drink.

Different groups of mice are constituted depending on the treatments: controls (injected with saline), prazosin 1 mg/kg, cyproheptadine 1 mg/kg, prazosin 1 mg/kg+cyproheptadine 1 mg/kg, prazosin 0.5 mg/kg+cyproheptadine 1 mg/kg, The tests begin 24 hours after forced alcoholization is stopped. They proceed during the first two hours of darkness (period of activity), during which the animals have access to a feeder with water and a feeder with alcohol. The amounts of water and of alcohol consumed are measured after said two hours.

Several sessions of measuring the consumption of water and of alcohol are carried out. For the first 2 sessions (S1-S2) the animals receive an injection of saline; they receive the treatments (prazosin, cyproheptadine, prazosin+cyproheptadine) or saline (for the control group) in the next sessions (T1, T2, T3). The treatments are carried out 10 minutes before each session.

The Alcohol/Water preference index (Pref.) is calculated as follows:

$$\text{Pref.} = (\text{Consumption Alcohol} - \text{Water})/(\text{Consumption Alcohol} + \text{Water})$$

$0 < \text{Pref.} \leq 1$: Preference for alcohol
$\text{Pref.} = 0$: No preference alcohol vs water
$-1 \leq \text{Pref.} < 0$: Preference for water (i.e. aversion to alcohol)

During the sessions for measuring alcohol consumption, the animals receive the treatments 30 minutes before said measurement.

The results are expressed in mean value and standard error of mean (SEM). The preference indices (Pref) of the treated groups are compared with that of the control group by the bilateral Student t-test for independent groups. The values shown (p vs Con) are the probabilities for the difference between treated group and control group being due to chance. A difference is regarded as statistically significant if $p \leq 0.05$.

Results

Experiment A

TABLE A

Effect of treatment with cyproheptadine and prazosin on alcoholic preference
(n = 6 animals per group)

| | | S-2 | S-1 | T1 | T2 | T3 |
|---|---|---|---|---|---|---|
| Control | Mean | 0.69 | 0.86 | 0.67 | 0.94 | 1.00 |
| n = 6 | SEM | 0.14 | 0.14 | 0.15 | 0.06 | 0.00 |
| Cyproheptadine (1 mg/kg) | Mean | 0.84 | 0.78 | 0.92 | 0.82 | 0.82 |
| n = 6 | SEM | 0.10 | 0.10 | 0.08 | 0.12 | 0.12 |
| | p vs Con | 0.43 | 0.66 | 0.17 | 0.37 | 0.16 |
| Prazosin (1 mg/kg) | Mean | 0.68 | 0.61 | 0.78 | 0.57 | 0.72 |
| n = 6 | SEM | 0.12 | 0.13 | 0.22 | 0.15 | 0.18 |
| | p vs Con | 0.93 | 0.24 | 0.69 | 0.25 | 0.16 |

Pref. = (Consumption Alcohol - Water)/(Consumption Alcohol + Water)
S2 and S1: sessions of saline treatment for all the groups
T1, T2 and T3: sessions of treatment with cyproheptadine 1 mg/kg or prazosin 1 mg/kg, with the controls receiving saline.

These results indicate that, on this model and at the doses used, cyproheptadine and prazosin administered separately do not have a significant effect on alcoholic preference.

Experiment B

TABLE B

Effect of treatment with cyproheptadine in combination with prazosin on alcoholic preference (n = 6 or 9 animals per group)

|  |  | S-2 | S-1 | T1 | T2 | T3 |
|---|---|---|---|---|---|---|
| Control | Mean | 0.69 | 0.86 | 0.94 | 1.00 | 1.00 |
| n = 6 | SEM | 0.14 | 0.14 | 0.06 | 0.00 | 0.00 |
| Cyproheptadine (1 mg/kg)/ Prazosin (0.5 mg/kg) | Mean | 0.81 | 0.94 | −0.37 | −0.70 | −0.81 |
| n = 9 | SEM | 0.10 | 0.06 | 0.21 | 0.15 | 0.13 |
|  | p vs Con | 0.62 | 0.52 | 0.0002 | 0.0001 | 0.0001 |
| Cyproheptadine (1 mg/kg)/ Prazosin (1 mg/kg) | Mean | 0.79 | 0.82 | −0.25 | −0.56 | −0.83 |
| n = 6 | SEM | 0.11 | 0.12 | 0.36 | 0.20 | 0.17 |
|  | p vs Con | 0.62 | 0.85 | 0.04 | 0.0001 | 0.0001 |

Pref. = (Consumption Alcohol - Water)/(Consumption Alcohol + Water)
S2 and S1: sessions with saline treatment
T1, T2 and T3: sessions of treatment with cyproheptadine 1 mg/kg in combination with prazosin 0.5 mg/kg or 1 mg/kg. The control group receives an administration of saline, as in sessions S1 and S2.

These results indicate that, on this model and at these doses, cyproheptadine and prazosin administered in combination have a significant effect on alcoholic preference. It will be noted that this combination leads to a strong aversion to alcohol (Preference negative, approaching −1), regardless of the prazosin dose.

A synergy of action between cyproheptadine and prazosin is therefore demonstrated.

Experiment C

TABLE C

Effect of treatment with cyproheptadine in combination with ifenprodil on alcoholic preference (n = 6 or 9 animals per group)

|  |  | S1 | S2 | T1 | T2 | T3 |
|---|---|---|---|---|---|---|
| Controls (n = 12) | Mean | 0.91 | 0.92 | 0.95 | 0.96 | 0.92 |
|  | SEM | 0.070 | 0.054 | 0.360 | 0.042 | 0.056 |
| Ifenprodil (1 mg/kg) + cyproheptadine (1 mg/kg) | Mean | 0.93 | 0.95 | 0.75 | 0.08 | 0.00 |
|  | SEM | 0.067 | 0.950 | 0.123 | 0.104 | 0.089 |
|  | p vs Con | 0.79564 | 0.72327 | 0.06208 | 0.00000009 | 0.000000014 |

Pref = (Consumption Alcohol - Water)/(Consumption Alcohol + Water)
S2 and S1: sessions with saline treatment
T1, T2 and T3: sessions of treatment with cyproheptadine 1 mg/kg in combination with ifenprodil 1 mg/kg. The control group receives an administration of saline, as in sessions S1 and S2.

These results indicate that:
treatment with an ifenprodil+cyproheptadine composition is effective for reducing alcohol consumption in this model, and this effect increases as the sessions proceed;
but in comparison with the treatment with a cyproheptadine+prazosin composition, the cyproheptadine+ifenprodil composition is less effective, as the latter does not trigger aversion such as can be seen with the negative values of P induced by the cyproheptadine/prazosin combination (see results for example B above).

Conclusion

Prazosin and cyproheptadine administered separately do not have any effect on alcohol consumption, whereas in the same model and at the same doses, prazosin and cyproheptadine administered in combination significantly reduce alcohol consumption, which is characteristic of synergy between the compounds.

Prazosin and cyproheptadine, administered in combination at doses that do not have a major incapacitating effect, reduce preference for alcohol very significantly, to the point of triggering aversion. This effect is greater than the effects of the combination of ifenprodil and cyproheptadine described as effective in models of dependence on psychostimulants in patent application WO 2006/018538.

Moreover, the effect of the prazosin/cyproheptadine composition on alcohol consumption increases with the administrations, regardless of the doses used. This result means that chronic treatment can be considered favorably, with a possibility of modulating, or even limiting the doses.

These results finally indicate that the prazosin/cyproheptadine composition can counteract the appetitive effects of the various addictive substances, and consequently reduce the states of dependence.

EXAMPLE 2

The cyproheptadine/alfuzosin, cyproheptadine/terazosin and cyproheptadine/tamsulosin combinations were tested in experimental conditions identical to those described in example 1 above and using the same model.

The results obtained are presented in Table D below.

TABLE D

Effect of treatment with cyproheptadine in combination with alfuzosin, terazosin or tamsulosin on alcoholic preference
(n = 6 or 9 animals per group)

|  |  | S-2 | S-1 | T1 | T2 | T3 |
|---|---|---|---|---|---|---|
| Control (n = 6) | Mean | 0.54 | 0.63 | 0.72 | 0.84 | 0.97 |
| Cyproheptadine (1 mg/kg) (n = 9) | Mean | 0.66 | 0.68 | 0.91 | 0.76 | 0.81 |
| Alfuzosin (0.5 mg/kg) (n = 9) | Mean | 0.72 | 0.74 | 0.59 | 0.62 | 0.63 |
| Terazosin (0.5 mg/kg) (n = 9) | Mean | 0.65 | 0.81 | 0.64 | 0.75 | 0.72 |
| Tamsulosin (0.5 mg/kg) (n = 9) | Mean | 0.71 | 0.73 | 0.68 | 0.79 | 0.77 |
| Cyproheptadine (1 mg/kg) + alfuzosin (0.5 mg/kg) (n = 9) | Mean | 0.83 | 0.91 | −0.48 | −0.84 | −0.87 |
| Cyproheptadine (1 mg/kg) + terazosin (0.5 mg/kg) (n = 9) | Mean | 0.68 | 0.83 | −0.13 | −0.68 | −0.76 |
| Cyproheptadine (1 mg/kg) + tamsulosin (0.5 mg/kg) (n = 9) | Mean | 0.74 | 0.87 | −0.17 | −0.45 | −0.73 |

Pref = (consumption alcohol - water)/(consuniption alcohol + water)
S-1 and S-2 = treatment with a saline solution for all groups
T1, T2 and T3 = treatment with the products; the control group receives a saline solution

CONCLUSION

Cyproheptadine, alfuzosin, terazosin and tamsulosin administered separately do not have an effect on alcohol consumption, whereas on the same model and at the same doses, the cyproheptadine/alfuzosin, cyproheptadine/terazosin and cyproheptadine/tamsulosin combinations significantly reduce alcohol consumption, which is characteristic of a synergy between the compounds.

This effect is greater than the effects of the combination of ifenprodil and cyproheptadine described as effective in models of dependence on psychostimulants in patent application WO 2006/018538 (see example 1 above).

These results also indicate that, on this model and at these doses, the cyproheptadine/alfuzosin, cyproheptadine/terazosin and cyproheptadine/tamsulosin combinations have a significant effect on alcoholic preference. It will be noted that these combinations lead to strong aversion to alcohol (Preference negative, approaching −1), regardless of the combination.

Synergy of action between cyproheptadine and alfuzosin, terazosin or tamsulosin is demonstrated.

The invention claimed is:

1. A pharmaceutical composition for treating alcohol dependence in humans comprising only two active ingredients:
    a first of the active ingredients is a compound having an antagonistic action on the 5-HT2 serotoninergic receptors selected as being cyproheptadine in the amount of 0.4 to 20 mg; and
    a second of the active ingredients is a compound having an antagonistic action on the alpha1-noradrenergic receptors selected as being prazosin in the amount of 0.25 to 20 mg, wherein the first and second active ingredients are administered to a patient in need thereof to treat alcohol dependence.

2. The pharmaceutical composition as claimed in claim 1 for administration 1 to 4 times daily to an alcohol-dependent patient.

3. The pharmaceutical composition as claimed in claim 1 for daily administration 1 to 7 days per week to an alcohol-dependent patient.

4. A pharmaceutical product comprising only two active ingredients:
    a first of the active ingredients is a compound having an antagonistic action on the 5-HT2 serotoninergic receptors selected as being cyproheptadine in the amount of 0.4 to 20 mg; and
    a second of the active ingredients is a compound having an antagonistic action on the alpha1-noradrenergic receptors selected as being prazosin in the amount of 0.25 to 20 mg,
    as a combination product for treating alcohol dependence in humans.

5. A method for treating for treating alcohol dependence in humans comprising administering to a patient in need thereof a pharmaceutical composition comprising only two active ingredients, wherein a first of the active ingredients is a compound having an antagonistic action on the 5-HT2 serotoninergic receptors selected as being cyproheptadine in the amount of 0.4 to 20 mg; and a second of the active ingredients is a compound having an antagonistic action on the alpha1-noradrenergic receptors selected as being prazosin in the amount of 0.025 to 20 mg.

6. The method of claim 5 wherein the composition is administered 1 to 4 times daily to the patient.

7. The method of claim 5 wherein the composition is administered daily 1 to 7 days per week to the patient.

8. The method of claim 5 wherein the two active ingredients are administered in a single dose.

* * * * *